(12) United States Patent
Howard et al.

(10) Patent No.: US 6,800,792 B1
(45) Date of Patent: Oct. 5, 2004

(54) COMMERCIAL PRODUCTION OF LACCASE IN PLANTS

(75) Inventors: John A. Howard, College Station, TX (US); Elizabeth Hood, College Station, TX (US); Joseph Jilka, College Station, TX (US)

(73) Assignees: ProdiGene Inc., College Station, TX (US); Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/786,960
(22) PCT Filed: Oct. 5, 1999
(86) PCT No.: PCT/US99/23256
§ 371 (c)(1), (2), (4) Date: Mar. 12, 2001
(87) PCT Pub. No.: WO00/20615
PCT Pub. Date: Apr. 13, 2000

Related U.S. Application Data
(60) Provisional application No. 60/103,031, filed on Oct. 5, 1998.

(51) Int. Cl.$^7$ .................. C12N 15/09; C12N 15/31; C12N 15/82; A01H 5/00
(52) U.S. Cl. ............. 800/278; 800/298; 800/295; 800/287; 800/320.1; 800/320; 800/317; 800/288; 435/69.1; 435/468
(58) Field of Search .................. 800/278, 287, 800/298, 295, 320, 320.1, 317, 288; 435/69.1, 468, 419, 320.1; 536/23.7, 23.2, 24.1

(56) References Cited

U.S. PATENT DOCUMENTS

| | | |
|---|---|---|
| 5,480,801 A | 1/1996 | Wahleithner et al. |
| 5,618,482 A | 4/1997 | Olesen et al. |
| 5,667,531 A | 9/1997 | Yaver et al. |
| 5,693,506 A | 12/1997 | Rodriguez |
| 5,770,418 A | 6/1998 | Yaver et al. |

FOREIGN PATENT DOCUMENTS

| | | |
|---|---|---|
| DE | 9752666 | 7/1999 |
| WO | WO9709431 | 3/1997 |
| WO | WO9745549 | 12/1997 |
| WO | WO9811205 | 3/1998 |
| WO | WO0005381 | 2/2000 |

OTHER PUBLICATIONS

Broun et al. Science, vol. 282, pp. 131–133, 1998.*
Lazar et al. Molecular and Cellular Biology, vol. 8(3), pp. 1247–1252, 1988.*
Becker et al. Ann. Proc. Cytochem Soci. of Europe, pp. 325–331, 1993.*
Ong, Edgar, et al.; "Cloning and sequence analysis of two laccase complementary DNA's from the ligninolytic basidiomycete *Trametes versicolor*.", Gene;196:113–119 (1997).
Crestini, Claudia, et al.; "The early biodegeneration pathways of residual kraft lingin model compounds with laccase.", ISWPC (1997).
Bourbonnais, Robert, et al.; "Enzymatic delignification of craft pulp using laccase and a mediator", Tappi Journal, vol. 79: No. 6, Jun. (1996) p. 199–204.
Saloheimo, Markku, et al.; "Heterologous production of a ligninolytic enzyme: expression of the *Phlebia radiata* laccase gene in *Trichoderma reesei*", Bio/Thechnology vol. 9, Oct. 1991 p. 987–990.
Bourbonnais, Robert, et al.; "Lignin Oxidation by Laccase Isozymes from *Trametes versicolor* and role of the Mediator 2,2' –Azinobis(3–Ethylbenzthiazoline–6–Sulfonate) in Kraft Lignin Depolymerization", Applied and Environmental Microbiology, May 1995, p. 1876–1880; vol. 61, No. 5.
Berka, Randy, et al.; "Characterization of the gene encoding an extracellular laccase of *Myceliophthora thermophila* and analysis of the recombinant enzyme expressed in *Aspergillus oryzae*", Applied and Environmental Microbiology, Aug. 1997, p. 3151–3157; vol. 63, No. 8.
Call, H.P., et al.; "History, overview and applications of mediated lignolytic systems, especially laccase–mediator systems (Lignozym–process)", Journal of Biotechnology 53 (1997) P. 163–202.
Yaropolov, A.I., et al.; "Laccase: Properties, Catalytic Machanism, and Applicability", Applied Biochemistry and Biotechnology vol. 49, 1994 p. 257–280.
Amann, et al.; "The Lignozym Process—Coming closer to the Mill", 1997 ISWPC.
"Technical and Market Opportunities for glued wood products", Adhesives Age May 31, 1996 p.6–9.
Archibald, F.S., et al.; "Kraft pulp bleaching and delignification by *Trametes versicolor*.", Journal of Biotechnology, vol. 53 (1997) p. 215–236.
Solomon, Edward, et al.; "Multicopper Oxidases and Oxygenases", Chem. Rev 1996, 96, 2536–2605.

* cited by examiner

Primary Examiner—Ashwin Mehta
Assistant Examiner—Medina A. Ibrahim
(74) Attorney, Agent, or Firm—Patricia A. Sweeney

(57) ABSTRACT

Expression of laccase in plants at commercial levels of production is provided. The laccase gene is preferably operably linked with promoter sequences preferentially directing expression of laccase to the seed of the plant, and may additionally include sequences directing expression to the plant cell wall. Methods of improving the process of introducing DNA into plants via Agrobacterium are also provided.

19 Claims, 4 Drawing Sheets

COMMERCIAL PRODUCTION OF LACCASE IN PLANTS

This application is a 35 U.S.C. §371 national filing from PCT/US99/23256 filed Oct. 5, 1999 which claims priority to provisional application USSN 60/103,031, filed Oct. 5, 1998. These applications are incorporated herein by reference in their entirety.

BACKGROUND OF THE INVENTION

Laccase is an enzyme that is a blue copper oxidase. It is believed to have been first obtained from the Japanese tree Rhus venicifera. Yshida, H., Zur Chemie des urushi-Firniss, *J. Chem. Soc.* (Tokyo) 43, 472, 1883. It has since been found in a number of higher plants, but not at high levels. The main source of laccase for commercial purposes is fungi. White rot fungi Phanerochaete chrysosporium and Trametes (Coriolus) versicolor are common commercial sources of the enzyme. Other fungi producing laccase include Polyporus, Pleurotus, Philota, Neurospora, Podospora and Aspergillus.

The enzyme has a number of uses. Examples include catalyzing the oxidation of compounds such as o,p-diphenols, aminophenols, polyphenols, polyamines and inorganic ions. (See, e.g. Yaropolov et al., "Laccase Properties, Catalytic Mechanism, and Applicability" *Applied Biochemistry and Biotechnology* 49:257–280 (1994)). Its' use as a marker enzyme in enzyme immunoassay (EIA) has also been discussed, as well as its' use in oxidation of steroids and synthesis of vinblastine, a cytostatic compound used in treating malignant diseases.

The most common use of laccase, however, is in connection with the paper and pulp industry. Lignin is a rigid organic polymer and harsh physicochemical conditions must be used to attack or modify the substance. One answer in the search for means to break down lignin was found in the white rot fungi which can naturally destroy lignin, using laccase. In plants, laccase is localized in woody tissues and cell walls of herbaceous species and it is believed it participates in lignin biosynthesis. It is involved in breaking down lignin as well as creating lignin polymers. It is also especially useful as a "biological glue" when manufacturing glued wood products. Such products include construction and industrial plywood, oriented strand board, particleboard and medium density fiberboard.

Currently, the adhesive used is either a urea-formaldehyde type or a phenol-formaldehyde resin. There are disadvantages associated with use of formaldehyde in producing such products. Processing and end use monitoring are required as the levels of formaldehyde cannot exceed certain controls. Thus, there has been considerable interest in using such natural alternatives as laccase. It is reported that more than 1.2 million metric tons of adhesive resin solids are used to bond glued wood products in the United States. Which adhesive is used is driven by cost per unit of production, process compatibility and end-use durability. See, "Technical and Market Opportunities for Glued Wood Products" *Adhesive Age* May 31, 1996 V39, N6 p.609.

An example of such a process is described by Kharazipour et al in U.S. Pat. No. 5,505,772 and by Olesen et al. at U.S. Pat. No. 5,618,482. In general, fibers and chips from wood or wood-like materials are defibrated by mechanical, steam, or other process. Laccase is then brought into contact with the material in a solution which may contain various auxiliary elements. Since laccase is a large molecule, a mediator may be utilized to aid the enzyme in penetrating the wood and may be added to the solution. The mix is incubated and may then be shaped into formed boards.

A problem with using laccase produced by white-rot fungi, however, is that it is produced in relatively low amounts. Saloheimo, M. and Niku-Paavola, M-L. "Heterologous Production of a Ligninolytic Enzyme: Expression of the *Phlebia radiata* Laccase gene in *Trichoderma reesei*" *Bio/Technology* 9:987–990 (1991). Native expression is described at about 10,000 U/liter from *Trametes versicolor* after induction, which is about 220–250 mg/liter if all was laccase I, and about 65–75 mg/liter if the laccase was laccase II. Bourbonnais et al. *Appl. Environ. Microb.* 61, no.5 pp.1876–1880 (May 1995). Other experiments have shown expression in *Myceliophthora thermophila* and in *Aspergillus oryzae* was at about 5 mg/liter. Measurements by the inventors reflect that the natural laccase expression in plants is about less than 0.001% of soluble plant protein. Attempts by Saloheimo and Niku-Paavola to improve on these levels by using heterologous expression yielded 20 mg/l secreted active laccase. Berka et al. noted that expression levels are too low for commercial purposes. Berka et al. *Applied and Environmental Microbiology* p.3151–3157 (August 1997). While others have attempted to introduce laccase-encoding nucleotide sequences into plants for the purpose of changing the lignin content of the plant in WO 98/11205 and WO97/45549, they do not teach production of laccase at commercially acceptable levels for extraction and use.

The inventors have discovered that it is possible to produce commercially acceptable quantities of laccase in plants. This results in a considerable decrease in cost of producing the enzyme. Thus it is an object of the invention to produce laccase in plants at commercially useful levels.

Finally, also provided are improvements on methods of transforming these and other plants using Agrobacterium. Modifications to selection of the bacterial strain used, and of processing the strain are provided.

These and further objectives will become apparent from the description.

All references cited herein are incorporated herein by reference.

SUMMARY OF THE INVENTION

Plants and a process of using them is described in which commercial levels of laccase are produced in plants. Improvements to Agrobacterium-mediated transformation processes are also provided.

DETAILED DESCRIPTION OF THE PREFERRED EMBODIMENTS

Figure 1:
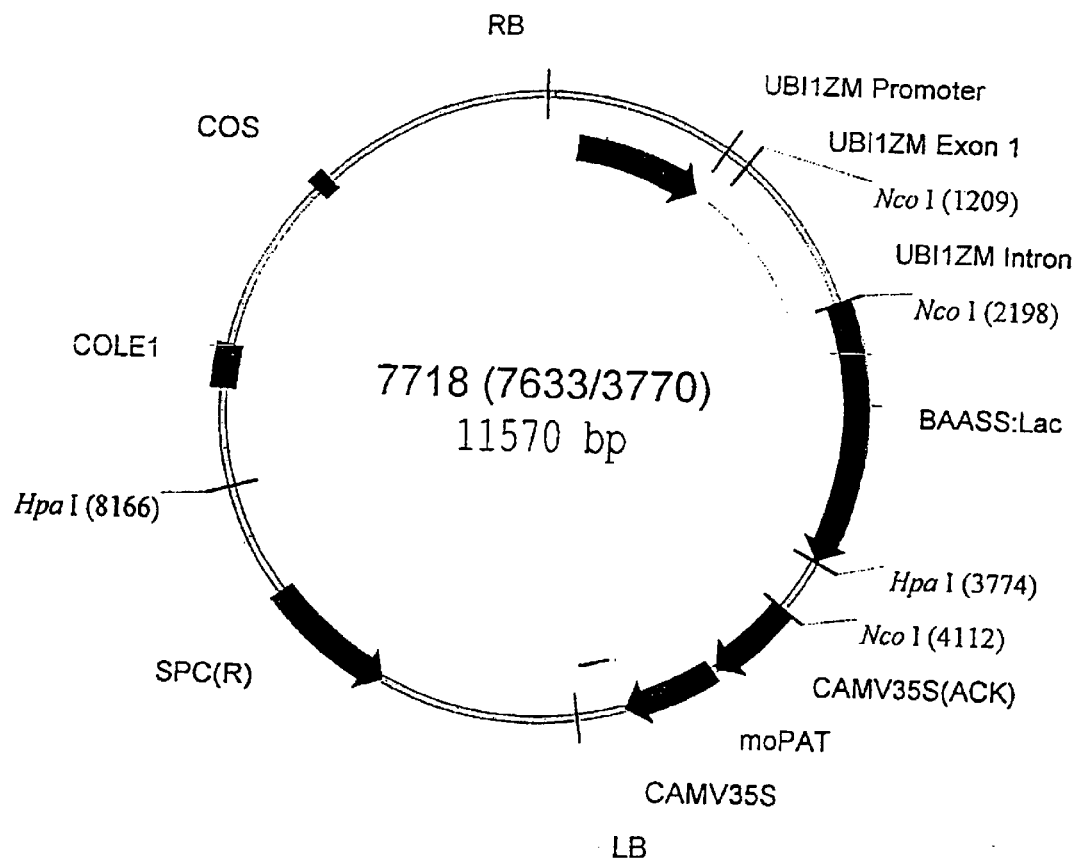
FIG. 1 is p7718, a construct containing the laccase gene driven by the ubiquitin promoter, containing the barley alpha amylase sequence and the maize optimized PAT gene as a selectable marker, driven by 35S promoter. It further contains left and right borders of the t-DNA sequences.

It has been determined by the inventors that commercial production of laccase in plants is feasible and provides considerable advantages over prior attempts to produce the enzyme from fungi. The level of production in plants according to the invention described herein is at a level which makes it economically advantageous to produce large quantities of the enzyme. Plants are easier to store, more economical to grow, more easily transported and can be far more readily produced in large quantities than can fungi, allowing for even further increases in the amount of enzyme which may be produced.

In accordance with the present invention, a DNA molecule comprising a transformation/expression vector is engineered to incorporate laccase-encoding DNA. Genes encoding this enzyme are well known. Some examples include the gene of laccase I cloned from *Aspergillus nidulans* as reported in Aramayo and Timberlake, *Nucleic Acids Res.* 18:3415 (1990); a laccase gene from *Phlebia radiata* and *Trichoderma reesei* described by Salohemo and Nicku-Paavola, supra; expressed in another fungus; a gene from *Myceliophthora termophila* is discussed by Berka et al, supra and expressed in another fungus; a laccase gene from eucalyptus and pine for use in controlling lignin content in the plants is described in PCT/NS97/00112; a laccase-encoding tobacco gene is shown to also be used in controlling lignin content of the transformed plant at WO 97/45549; a laccase-encoding gene corresponding to a *Rhizoctonia solani* gene is set forth in U.S. Pat. No. 5,480,801 and expressed in a microbe; and a gene from a basidiomycete, *Polyporus pinsitus* is discussed in U.S. Pat. No. 5,667,531, also expressed in a transformed microbe. The gene used in the present invention is from *Trametes versicolor*. Therefore, a gene for use in the present invention can be subcloned in a vector of choice.

In another example of DNA isolation, it is possible to screen a cDNA library with anti-laccase antibodies. The known methodologies used would include identification of the gene by hybridization with probes, PCR, probe/promoter/synthetic gene synthesis, sequencing, molecular cloning and other techniques which are well known to those skilled in molecular biology. While it is possible to synthesize the gene to reflect preferred codon usage in plants, and may be useful in increasing expression of laccases, (See, Murray et al, *Nucleic Acid Res.* 17:477–498 (1980)), it may not be necessary in all cases, as was found with the gene used in the examples below.

In addition to the exemplified laccase DNA and proteins taught herein, the present invention contemplates the utilization of homologous or substantially identical DNA sequences or proteins. The term "identical" in the context of two polypeptide or nucleic acid sequences refers to the residues in the two sequences that are the same when aligned for maximum correspondence, as measured using one of the following "sequence comparison algorithms." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a cellulase nucleic acid of this invention if the smallest sum probability in a comparison of the test nucleic acid to a cellulase nucleic acid is less than about 0.1, more preferably less than about 0.01, and most preferably less than about 0.001. Where the test nucleic acid encodes a cellulase polypeptide, it is considered similar to a specified cellulase nucleic acid if the comparison results in a smallest sum probability of less than about 0.5, and more preferably less than about 0.2.

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

In a preferred embodiment of the invention, expression of the enzyme in the plant may be increased by directing expression to the cell wall. This may be accomplished by use of a signal sequence and in a preferred embodiment is the barley alpha amylase signal sequence, Rogers, *J. Biol. Chem.* 260:3731–3738 (1985), or brazil nut protein signal sequence when used in canola or other dicot. Another alternative is to express the enzyme in the endoplasmic reticulum of the plant cell. This may be accomplished by use of a localization sequence, such as KDEL. This sequence contains the binding site for a receptor in the endoplasmic reticulum. Munro, S. and Pelham, H. R. B. 1987 "A C-terminal signal prevents secretion of luminal ER proteins." *Cell*. 48:899–907. The use of such a localization sequence will increase expression over levels obtained when the enzyme is otherwise expressed in the cytoplasm.

The methods available for putting together such a relatively short synthetic gene comprising the various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene has been isolated and engineered to contain some or all of the features described above, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the laccase; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker which is functionally linked to a promoter that controls transcription initiation. For a general description of plant expression vectors and reporter genes, see Gruber et al, "Vectors for Plant Transformation" in *Methods of Plant Molecular Biology aid Biotechnology* 89–119 (CRC Press, 1993).

Promoter elements employed to control expression of the laccase and the selection gene, respectively, can be any plant-compatible promoter. Those can be plant gene promoters, such as, for example, the ubiquitin promoter, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al, *Science* 236:1299 (1987) and European patent application No. 0 342 926. See international application WO 91/19806 for a review of illustrative plant promoters suitably employed in the present invention. The range of available plant compatible promoters includes tissue specific and inducible promoters.

In one embodiment of the present invention, the exogenous DNA is under the transcriptional control of a plant ubiquitin promoter. Plant ubiquitin promoters are well known in the art, as evidenced by European patent application no. 0 342 926.

In a further preferred embodiment, a tissue specific promoter is provided to direct transcription of the DNA preferentially to the seed. One such promoter is the globulin promoter. This is the promoter of the maize globulin-1 gene, described by Belanger, F. C. and Kriz, A. L. at "Molecular Basis for Allelic Polymorphism of the Maize Globulin-1 gene" *Genetics* 129:863–972 (1991). It also can be found as accession number L22344 L22295 in the Genebank database and is set forth below.

Obviously, many variations on the promoters, selectable markers and other components of the construct are available to one skilled in the art.

In accordance with the present invention, a transgenic plant is produced that contains a DNA molecule, comprised of elements as described above, integrated into its genome so that the plant expresses a heterologous laccase-encoding

```
                         Globulin promoter

Promoter:  1..1386
   TATA_signal:  1354..1360
   5'UTR         1387..1401
Base court:   423 a   308 c   272 g   398 t 1 aagcttgccg agtgccatcc ttggacactc gataaagtat attttatttt ttttattttg 61 ccaaccaaac tttttgtggt atgttcctac actatgtaga tctacatgta ccattttggc 121 acaattacat atttacaaaa atgttttcta taaatattag atttagttcg tttatttgaa 181 tttcttcgga aaattcacat ttaaactgca agtcactcga aacatggaaa accgtgcatg 241 caaaataaat gatatgcatg ttatctagca caagttacga ccgatttcag aagcagacca 301 gaatcttcaa gcaccatgct cactaaacat gaccgtgaac ttgttatcta gttgtttaaa 361 aattgtataa aacacaaata aagtcagaaa ttaatgaaac ttgtccacat gtcatgatat 421 catatataga ggttgtgata aaaatttgat aatgtttcgg taaagttgtg acgtactatg 481 tgtagaaacc taagtgacct acacataaaa tcatagagtt tcaatgtagt tcactcgaca 541 aagactttgt caagtgtccg ataaaaagta ctcgacaaag aagccgttgt cgatgtactg 601 ttcgtcgaga tctctttgtc gagtgtcaca ctaggcaaag tctttacgga gtgtttttca 661 ggctttgaca ctcggcaaag cgctcgattc cagtagtgac agtaatttgc atcaaaaata 721 gctgagagat ttaggccccg tttcaatctc acgggataaa gtttagcttc ctgctaaact 781 ttagctatat gaattgaagt gctaaagttt agtttcaatt accaccatta gctctcctgt 841 ttagattaca aatggctaaa agtagctaaa aaatagctgc taaagtttat ctcgcgagat 901 tgaaacaggg ccttaaaatg agtcaactaa tagaccaact aattattagc tattagtcgt 961 tagcttcttt aatctaagct aaaaccaact aatagcttat ttgttgaatt acaattagct 1021 caacggaatt ctctgttttt ctaaaaaaaa actgcccctc tcttacagca aattgtccgc 1081 tgcccgtcgt ccagatacaa tgaacgtacc tagtaggaac tcttttacac gctcggtcgc 1141 tcgccgcgga tcggagtccc cggaacacga caccactgtg gaacacgaca aagtctgctc 1201 agaggcggcc acacccctgg gtgcaccgag ccggagcccg gataagcacg gtaaggagag 1261 tacggcggga cgtggcgacc cgtgtgtctg ctgccacgca gccttcctcc acgtagccgc 1321 gcggccgcgc cacgtaccag ggcccggcgc tggtataaat gcgcgccacc tccgctttag 1381 ttctgcatac agccaaccca a
```

Another example is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" *The Plant Cell* Vol. 1, 839–853 (1989).

In another preferred embodiment, the selective gene is a glufosinate-resistance encoding DNA and in a preferred embodiment can be the phosphinothricin acetyl transferase ("PAT") or maize optimized PAT gene under the control of the CaMV 35S promoter. The gene confers resistance to bialaphos. See, Gordon-Kamm et al, *The Plant Cell* 2:603 (1990); Uchimiya et al, *Bio/Technology* 11:835 (1993), and Anzai et al, *Mol. Gen. Gen.* 219:492 (1989).

DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al, "Procedures for Introducing Foreign DNA into Plants" in *Methods in Plant Molecular Biology and Biotechnology*, Glick et al (eds) pp. 67–68 (CRC Press 1993) and by Phillips et al, "Cell/Tissue Culture and In Vitro Manipulation" in *Corn and Corn Improvement* 3d Edit. Sprague et al (eds) pp. 345–387

(American Soc. Of Agronomy 1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al, *Bio/Technology* 10:268 (1992); and Weisinger et al., *Ann. Rev. Genet.* 22: 421–477 (1988). For example, the DNA construct may be introduced into the genomic DNA of the plant cell using techniques such as microprojectile-mediated delivery, Klein et al., *Nature* 327: 70–73 (1987); electroporation, Fromm et al., *Proc. Natl. Acad. Sci.* 82: 5824 (1985); polyethylene glycol (PEG) precipitation, Paszkowski et al., *Embo J.* 3: 2717–2722 (1984); direct gene transfer, WO 85/01856 and EP No. 0 275 069; in vitro protoplast transformation, U.S. Pat. No. 4,684,611; and microinjection of plant cell protoplasts or embryogenic callus. Crossway, *Mol. Gen. Genetics* 202:179–185 (1985). Co-cultivation of plant tissue with *Agrobacterium tumefaciens* is another option, where the DNA constructs are placed into a binary vector system. Ishida et al., "High Efficiency Transformation of Maize (*Zea mays* L.) Mediated by *Agrobacterium tumefaciens*" *Nature Biotechnology* 14:745–750 (1996). The virulence functions of the *Agrobacterium tumefaciens* host will direct the insertion of the construct into the plant cell DNA when the cell is infected by the bacteria. See, for example Horsch et al., *Science* 233: 496–498 (1984), and Fraley et al., *Proc. Natl. Acad. Sci.* 80: 4803 (1983).

Standard methods for transformation of canola are described by Moloney et al. "High Efficiency Transformation of *Brassica napus* Using Agrobacterium Vectors" *Plant Cell Reports* 8:238–242 (1989). Corn transformation is described by Fromm et al, *Bio/Technology* 8:833 (1990) and Gordon-Kamm et al, supra. Agrobacterium is primarily used in dicots, but certain monocots such as maize can be transformed by Agrobacterium. U.S. Pat. No. 5,550,318. Rice transformation is described by Hiei et al., "Efficient Transformation of Rice (*Oryza sativs* L.) Mediated by Agrobacterium and Sequence Analysis of the Boundaries of the T-DNA" *The Plant Journal* 6(2): 271–282 (1994), Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. Sorghum transformation is described by Casas et al, supra and by Wan et al, *Plant Physiolog.* 104:37 (1994). Soybean transformation is described in a number of publications, including U.S. Pat. No. 5,015,580.

In one preferred method, the Agrobacterium transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the High II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, it cannot survive in Agrobacterium without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing fresh culture of the Agrobacterium on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. "Establishment and maintenance of friable, embryogenic maize callus and involvement of L-proline" Planta (1985) 154:207–214. The resuspension medium is the same as that described above. All further Hi II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of laccase, and it is thus useful to ascertain expression levels in transformed plant cells, transgenic plants and tissue specific expression. One such method is an ELISA assay which uses biotinylated anti-laccase polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection.

The levels of expression of the gene of interest can be enhanced by the stable maintenance of a laccase encoding gene on a chromosome of the transgenic plant. Use of linked genes, with herbicide resistance in physical proximity to the laccase gene, would allow for maintaining selective pressure on the transgenic plant population and for those plants where the genes of interest are not lost.

With transgenic plants according to the present invention, laccase can be produced in commercial quantities. Thus, the selection and propagation techniques described above yield a plurality of transgenic plants which are harvested in a conventional manner. The plant with the laccase can be used in the processing, or the laccase extracted. When using the plant itself, it can, for example, be powdered and then applied in the commercial process, or the seed made into flour. Laccase extraction from biomass can be accomplished by known methods which are discussed, for example, by Heney and Orr, *Anal. Biochem.* 114: 92–96 (1981).

It is evident to one skilled in the art that there can be loss of material in any extraction method used. Thus, a minimum level of expression is required for the process to be economically feasible. For the relatively small number of transgenic plants that show higher levels of expression, a genetic map can be generated, via conventional RFLP and PCR analysis, which identifies the approximate chromosomal location of the integrated DNA molecule. For exemplary methodologies in this regard, see Glick and Thompson, in *Methods in Plant Molecular Biology and Biotechnology* 269–84 (CRC Press 1993). Genetic mapping can be effected, first to identify DNA fragments which contain the integrated DNA and then to locate the integration site more precisely. This further analysis would consist primarily of DNA hybridizations, subcloning and sequencing. The information thus obtained would allow for the cloning of a corresponding DNA fragment from a plant not engineered with a heterologous laccase gene. (Here, "corresponding" refers to a DNA fragment that hybridizes under stringent conditions to the fragment containing the laccase encoding gene). The cloned fragment can be used for high level expression of another gene of interest. This is accomplished by introducing the other gene into the plant chromosome, at a position and in an orientation corresponding to that of the heterologous gene. The insertion site for the gene of interest would not necessarily have to be precisely the same as that of the laccase gene, but simply in near proximity. Integration of an expression vector constructed as described above, into the plant chromosome then would be accomplished via recombination between the cloned plant DNA fragment and the chromosome. Recombinants, where the gene of interest resides on the chromosome in a position corresponding to that of the highly expressed laccase gene likewise should express the gene at high levels.

The laccase gene may also be included in a plant that contains one of the mediators that is useful in commercial application of laccase. Laccase is a large molecule, and hence when used in such processes as delignification, may be enhanced by the use of a mediator. It was found that fungi that degrade wood secrete low molecular weight compounds which act to allow penetration of the wood fibers. Mediators include 1-hydroxybenzotriazole (HBT), 2,2' azeno-bis-(3-ethylbenzothiazoline-6-sulfonic acid) (ABTS), 1-nitroso-2-naphthol-3,6-disulfonic acid (NNS) and chlorpromazine (CPZ), to name a few. One review of such mediators is found at M. Amann, "The Lignozyme Process-Coming Closer to the Mill" *International Symposium on Wood and Pulping Chemistry* $9^{th}$, Montreal, Technical Section, Canadian Pulp and Paper Association. Classes of enhancers are also described in WO 94/12619, WO 94/12620, WO 94/12621 and WO 98/23716. An overview of laccase and mediators is provided at H. P. Call, I. Mucke, *Journal of Biotechnology* (1997) 53:163–202.

Any method to combine the gene with the plant having the mediator will meet the goal, and the process used will vary depending upon the resources of the manufacturer, and the plants involved. By way of example, the laccase gene may be introduced directly into the plant, or a plant with the laccase gene may be backcrossed into the plant having the mediator substance. Backcrossing is a method in which a desirable trait is transferred from one plant into another plant which lacks the trait, but contains other desirable characteristics. By use of a selectable marker, presence of the laccase gene may be confirmed. The progeny is then crossed again to a plant having the mediator. This plant may be then used for generation of laccase and the mediator within the resulting plant, or further backcrossing may be used so that the resulting plant is like the mediator-containing plant in all aspects except that it contains the laccase gene.

The enzyme can be used in a number of different industrial processes. Examples include its use for an in-situ depolymerization of lignin in Kraft pulp, thereby producing a pulp with lower lignin content. Such methods are described in, for example, Jin et al, Holzforschung 45(6): 467–468, 1991; U.S. Pat. No. 4,432,921. This use of laccase is an improvement over the current use of chlorine for depolymerization of lignin, which leads to the production of chlorinated aromatic compounds, which are an environmentally undesirable by-product of paper mills. Such uses are described in, for example, Current Opinion in Biotechnology 3:261–266, 1992; J. Biotechnol. 25:333–339, 1992, Hiroi et al, Svensk papperstidning 5:162–166, 1976. Production of fibreboard is also possible using laccase, by adding it to a slurry of lignin-containing wood fiber material, forming a mat of the wood fiber material and pressing it by applying heat and pressure. See e.g. U.S. Pat. No. 5,618,482. As mentioned, supra, laccase can also substitute for less desirable adhesive resin solids to bond glued wood products. See Adhesives Age, supra. Its use as an adhesive includes construction and industrial plywood, oriented strand board, particleboard used for interior applications and medium density fiberboard. These are but a few of the many uses to which the enzyme may be put.

The following illustrates, but is not intended to limit the scope of the invention. It will be evident to one skilled in the art that variations and modifications are possible and fall within the scope and spirit of the invention.

Seed from Hi-II maize kernels were transformed with constructs comprising elements according to the present invention. The constructs are designated p7699, p7718, and p7017. The p7017 construct comprises the ubiquitin promoter, including the first exon and intron; the barley alpha amylase export signal sequence as well as the native fungal signal sequences; KDEL sequence; a laccase-encoding sequence; and the 35S promoter and terminator with the moPAT (maize optimized PAT selectable marker). The p7699 construct is essentially the same as p7017, but does not contain the fungal signal sequence. Construct p7718 contains the barley alpha amylase sequence, but not the fungal signal sequence nor KDEL.

The following provides further detail and is presented by way of illustration and is not intended to limit the scope or spirit of the invention.

EXAMPLE 1

Isolation and Cloning of Laccase Encoding DNA

The gene for laccase was cloned from Trametes versicolor by the methods described here, with isolated RNA reverse transcribed into cDNA. The sequence is set forth below

SEQUENCE ID NO. 1

```
       gccatcgggccggtggcgagcctcgtcgtcgcgaacgcccccgtctcgcccgacggcttc
  1    ------------------------------------------------------------+  60
       cggtagcccggccaccgctcggagcagcagcgcttgcgggggcagagcgggctgccgaag
       A  I  G  P  V  A  S  L  V  V  A  N  A  P  V  S  P  D  G  F cttcgggatgccatcgtggtcaacggcgtggtccctt ccccgctcatcaccgggaagaag
 61    ------------------------------------------------------------+ 120
       gaagccctacggtagcaccagttgccgcaccagggaaggggcgagtagtgggcccttcttc
       L  R  D  A  I  V  V  N  G  V  V  P  S  P  L  I  T  G  K  K ggagaccgcttccagctcaacgtcgtcgacaccttgaccaaccacagcatgctcaagtcc
121    ------------------------------------------------------------+ 180
       cctctggcgaaggtcgagttgcagcagctgtggaactggttggtgtcgtacgagttcagg
       G  D  R  F  Q  L  N  V  V  D  T  L  T  N  H  S  M  L  K  S actagtatccactggcacggcttcttccaggcaggcaccaactgggcagacggacccgcg
181    ------------------------------------------------------------+ 240
       tgatcataggtgaccgtgccgaagaaggtccgtccgtggttgacccgtctgcctgggcgc
       T  S  I  H  W  H  G  F  F  Q  A  G  T  N  W  A  D  G  P  A ttcgtcaaccagtgccctattgcttccgggcattcatttctgtacgacttccatgtgccc
241    ------------------------------------------------------------+ 300
       aagcagttggtcacgggataacgaaggcccgtaagtaaagacatgctgaaggtacacggg
       F  V  N  Q  C  P  I  A  S  G  H  S  F  L  Y  D  F  H  V  P gaccaggcaggaacgttctggtaccacagtcatctgtctacgcaatactgtgacgggctg
301    ------------------------------------------------------------+ 360
       ctggtccgtccttgcaagaccatggtgtcagtagacagatgcgttatgacactgcccgac
       D  Q  A  G  T  F  W  Y  H  S  H  L  S  T  Q  Y  C  D  G  L cgaggaccgttcgtcgtgtacgaccccaaggatccgcacgccagccgctacgatgttgac
361    ------------------------------------------------------------+ 420
       gctcctggcaagcagcacatgctgggttcctaggcgtgcggtcggcgatgctacaactg
       R  G  P  F  V  V  Y  D  P  K  D  P  H  A  S  R  Y  D  V  D aacgagagcacggtcatcacgttgaccgactggtaccacaccgctgcccggctcggtccc
421    ------------------------------------------------------------+ 480
       ttgctctcgtgccagtagtgcaactggctgaccatggtgtggcgacgggccgagccaggg
       N  E  S  T  V  I  T  L  T  D  W  Y  H  T  A  A  R  L  G  P aggttcccactcggcgcggacgccacgctcatcaatggtcttgggcggtcggcctccact
481    ------------------------------------------------------------+ 540
       tccaagggtgagccgcgcctgcggtgcgagtagttaccagaacccgccagccggaggtga
       R  F  P  L  G  A  D  A  T  L  I  N  G  L  G  R  S  A  S  T cccaccgccgcgcttgctgtgatcaacgtccagcacggaaagcgctaccgcttccgtctc
541    ------------------------------------------------------------+ 600
       gggtggcggcgcgaacgacactagttgcaggtcgtgccttt cgcgatggcgaaggcagag
       P  T  A  A  L  A  V  I  N  V  Q  H  G  K  R  Y  R  F  R  L gtttcgatctcgtgcgacccgaactacacgttcagcatcgacgggcacaatctgaccgtc
601    ------------------------------------------------------------+ 660
       caaagctagagcacgctgggcttgatgtgcaagtcgtagctgcccgtgttagactggcag
       V  S  I  S  C  D  P  N  Y  T  F  S  I  D  G  H  N  L  T  V atcgaggtcgacggtatcaacagccagcctctccttgtcgactctatccagatcttcgcc
661    ------------------------------------------------------------+ 720
       tagctccagctgccatagttgtcggtcggagaggaacagctgagataggtctagaagcgg
       I  E  V  D  G  I  N  S  Q  P  L  L  V  D  S  I  Q  I  F  A gcgcagcgctactcctttgtgttgaatgcgaaccaaacggtcggcaactactgggtccgc
721    ------------------------------------------------------------+ 780
       cgcgtcgcgatgaggaaacacaacttacgcttggtttgccagccgttgatgacccaggcg
       A  Q  R  Y  S  F  V  L  N  A  N  Q  T  V  G  N  Y  W  V  R
```

```
                -continued
    gcgaacccgaacttcggaacggttgggttcgccggggggatcaactccgccatcctgcgc
781 ---------+---------+---------+---------+---------+---------+ 840
    cgcttgggcttgaagccttgccacccaagcggcccccctagttgaggcggtaggacgcg
    A  N  P  N  F  G  T  V  G  F  A  G  G  I  N  S  A  I  L  R taccaaggcgcaccagtcgccgagcccactacgacccagacgacgtcggtgatcccgctt
841 ---------+---------+---------+---------+---------+---------+ 900
    atggttccgcgtggtcagcggctcgggtgatgctgggtctgctgcagccactagggcgaa
    Y  Q  G  A  P  V  A  E  P  T  T  T  Q  T  T  S  V  I  P  L atcgagacgaacttgcacccctcgctcgcatgcctgtgcctggcagcccgacacccggg
901 ---------+---------+---------+---------+---------+---------+ 960
    tagctctgcttgaacgtggggagcgagcgtacggacacggaccgtcgggctgtgggccc
    I  E  T  N  L  H  P  L  A  R  M  P  V  P  G  S  P  T  P  G ggcgtcgacaaggcgctcaacctcgcgtttaacttcaacggcaccaacttcttcatcaac
961 ---------+---------+---------+---------+---------+---------+ 1020
    ccgcagctgttccgcgagttggagcgcaaattgaagttgccgtggttgaagaagtagttg
    G  V  D  K  A  L  N  L  A  F  N  F  N  G  T  N  F  F  I  N aacgcgactttcacgccgccgaccgtcccggtactcctccagattctgagcggtgcgcag
1021 ---------+---------+---------+---------+---------+---------+ 1080
     ttgcgctgaaagtgcggcggctggcagggccatgaggaggtctaagactcgccacgcgtc
     N  A  T  F  T  P  P  T  V  P  V  L  L  Q  I  L  S  G  A  Q accgcacaagacctgctccctgcaggctctgtctacccgctcccggcccactccaccatc
1081 ---------+---------+---------+---------+---------+---------+ 1140
     tggcgtgttctggacgagggacgtccgagacagatgggcgagggccgggtgaggtggtag
     T  A  Q  D  L  L  P  A  G  S  V  Y  P  L  P  A  H  S  T  I gagatcacgctgcccgcgaccgccttggccccgggtgcaccgcacccttccacctgcac
1141 ---------+---------+---------+---------+---------+---------+ 1200
     ctctagtgcgacgggcgctggcggaaccggggcccacgtggcgtggggaaggtggacgtg
     E  I  T  L  P  A  T  A  L  A  P  G  A  P  H  P  F  H  L  H ggtcacgccttcgcggtcgttcgcagcgcggggagcaccacgtataactacaacgacccg
1201 ---------+---------+---------+---------+---------+---------+ 1260
     ccagtgcggaagcgccagcaagcgtcgcgcccctcgtggtgcatattgatgttgctgggc
     G  H  A  F  A  V  V  R  S  A  G  S  T  T  Y  N  Y  N  D  P atcttccgcgacgtcgtgagcacgggcacgcccgccgcgggcgacaacgtcacgatccgc
1261 ---------+---------+---------+---------+---------+---------+ 1320
     tagaaggcgctgcagcactcgtgcccgtgcgggcggcgcccgctgttgcagtgctaggcg
     I  F  R  D  V  V  S  T  G  T  P  A  A  G  D  N  V  T  I  R ttccagacggacaaccccgggccgtggttcctccactgccacatcgacttccacctcgac
1321 ---------+---------+---------+---------+---------+---------+ 1380
     aaggtctgcctgttggggcccggcaccaaggaggtgacggtgtagctgaaggtggagctg
     F  Q  T  D  N  P  G  P  W  F  L  H  C  H  I  D  F  H  L  D gcgggcttcgcgatcgtgttcgcagaggacgttgcggacgtgaaggcggcgaacccggtt
1381 ---------+---------+---------+---------+---------+---------+ 1440
     cgcccgaagcgctagcacaagcgtctcctgcaacgcctgcacttccgccgcttgggccaa
     A  G  F  A  I  V  F  A  E  D  V  A  D  V  K  A  A  N  P  V ccgaaggcgtggtcggacctgtgcccgatctacgacgggctgagcgaggctaaccagtga
1441 ---------+---------+---------+---------+---------+---------+ 1500
     ggcttccgcaccagcctggacacgggctagatgctgcccgactcgctccgattggtcact
     P  K  A  W  S  D  L  C  P  I  Y  D  G  L  S  E  A  N  Q  *
```

EXAMPLE 2

Preparation of Plasmids

Figure 4:
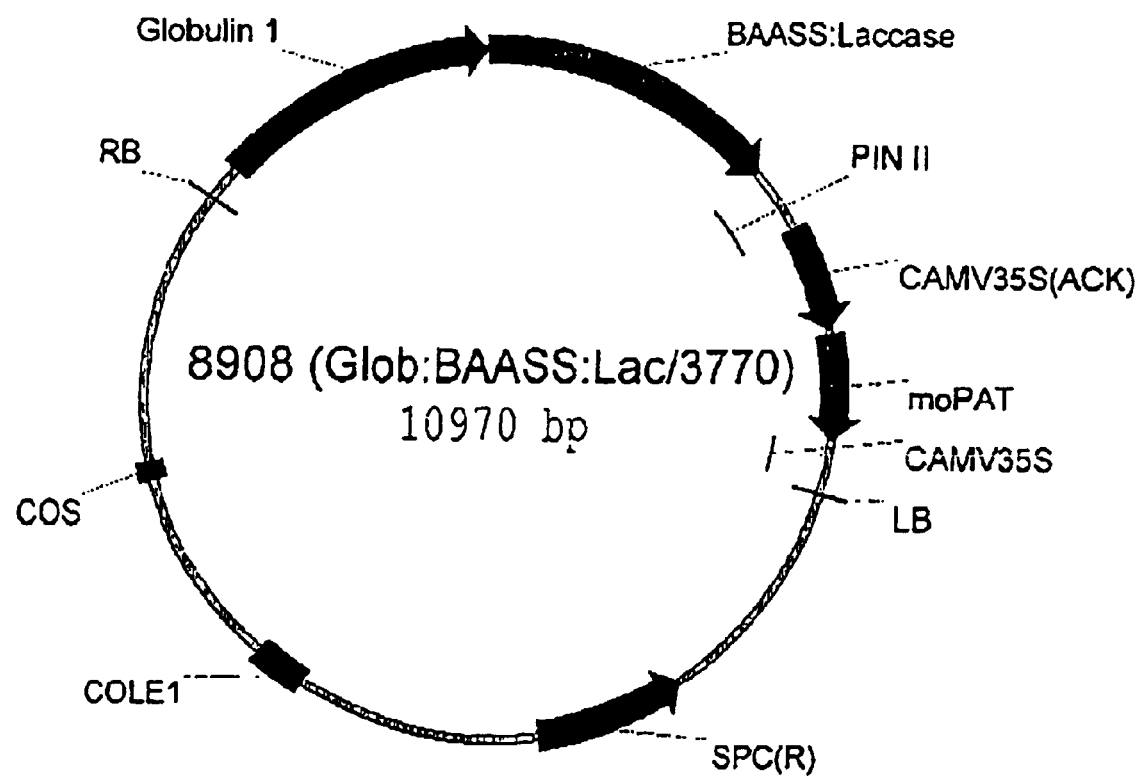
FIG. 4 is p8908, which is the same as 7718, except it substitutes the globulin promoter for the ubiquitin promoter.

The plasmids containing the barley alpha amylase signal sequences were produced by ligating oligomeric sequences encoding the sequence to the 5' end of the laccase gene, then the entire sequence amplified by PCR and cloned into a pCR™-TOPO vector, available from Invitrogen™. This vector is designed for cloning of TAQ amplified products, and has 3' T overhangs for direct ligation to TAQ amplified PCR products. Since TAQ adds extra A sequence to the 3' end, it links with the overhang in the vector. See e.g. U.S. Pat. No. 5,487,993. The sequencing of individual clones followed and confirmed the presence of the construct. An individual clone was chosen for further manipulations. To generate plasmid 7718 (FIG. 1) intermediate vectors with BAASS: laccase were cut with NcoI and HpaI and ligated into vector 2774, which contains the ubiquitin promoter and PinII terminator. The entire transcription unit was cut from 2774 with NheI and NotI and ligated to 3770 containing the 35S promoter with the PAT selectable marker between the left and right borders of the *Agrobacterium tumefaciens* gene. For plasmid 8908 (FIG. 4) the same procedure was employed, and the ubiquitin promoter of the 2774 vector removed, substituting the globulin promoter. The globulin promoter in p3303 was cut with HindIII and NcoI, and vector 2774 having the ubiquitin, barley alpha amylase, laccase and PinII sequences was cut with the same restriction enzymes. The two pieces were then ligated to create plasmid KB254. While there are several approaches possible for preparing the plasmid, in this procedure the HindIII and NarI site from KB254 was used to cut p7718 and substitute the globulin promoter for the ubiquitin promoter in 7718.

Figure 2:
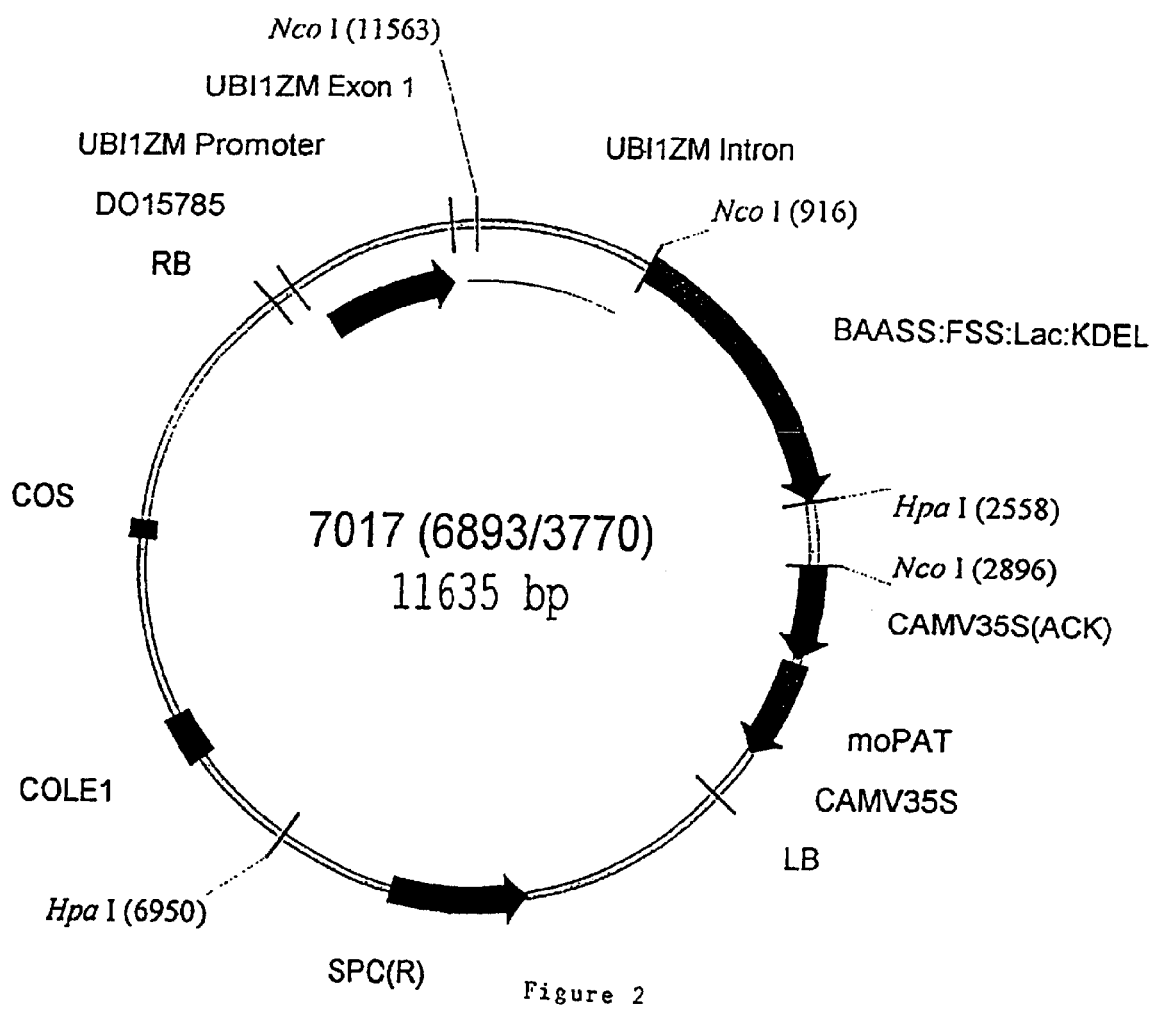
FIG. 2 is p7017, a construct which is essentially the same as p7718, except that it also contains the KDEL sequence and a fungal signal sequence.
Figure 3:
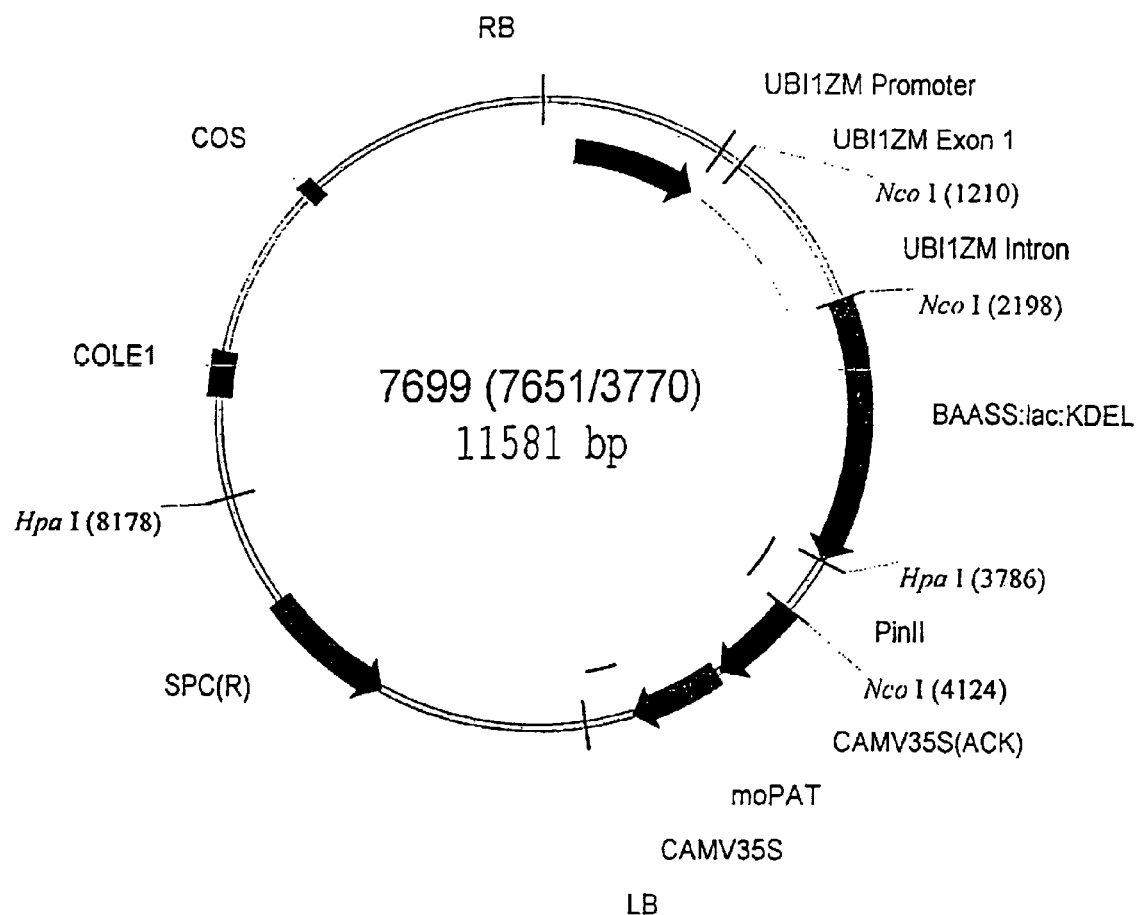
FIG. 3 is p7699, which is essentially the same as p7017, except that the fungal signal sequence is not present.

For plasmids 7017 and 7699, (FIGS. 2 and 3) containing the KDEL sequence, the nucleotides for the amino acids lysine, aspartic acid, glutamic acid and leucine (KDEL) were added to the 3' end of the laccase gene by PCR amplification using a reverse primer containing the KDEL sequence. The entire coding sequence is then put into 2774 containing the ubiquitin promoter and the PinII terminator. Following this it is cut with NheI and NotI and ligated to 3770 as described above, to generate 7017 and 7699.

EXAMPLE 3

Transformation of Maize

Fresh immature zygotic embryos were harvested from Hi-II maize kernels at 1–2 mm in length. The general methods of Agrobacterium transformation were used as described by Japan Tobacco, at Ishida, Y, H Saito, S Ohta, Y Hiei, T Komari and T Kumashiro. 1996. "High efficiency transformation of maize (*Zea mays* L.) mediated by *Agrobacterium tumefaciens*" *Nature Biotechnology* 14:745–750 with the modifications described supra. Fresh embryos were treated with 0.5 ml log phase Agrobacterium strains EHA 101. Bacteria were grown overnight in a rich medium with kanamycin and spectinomycin to an optical density of 0.5 at 600 nm, pelleted, then re-inoculated in a fresh 10 ml culture. The bacteria were allowed to grow into log phase and were harvested at no more dense than OD600=0.5. The bacterial culture is resuspended in a co-culture medium. For transient expression assays, embryos (5–10 per tube) were sonicated in the presence of the bacteria for 30 sec (Trick H and J Finer. 1997. "SAAT: sonication-assisted Agrobacterium-mediated transformation." *Transgenic Research* 6-329–336), then plated on a solid medium as above. Embryos and bacteria were co-cultivated for 5 days.

For stable transformations, embryos not subjected to sonication were transferred to a bialaphos selective agent on embryogenic callus medium and transferred thereafter every two weeks to allow growth of transformed type II callus. Plants were regenerated from the callus.

EXAMPLE 4

Detection of Expression of Laccase

The corn tissue was analyzed by a laccase activity assay and stable and transient expression of laccase confirmed.

Stable expression has been confirmed in p7718 and p7017. Most of the plants of p7699 died for unknown reasons. Assays described below confirmed expression of laccase at levels of 0.1% total soluble protein for plants with p7718 and levels of 0.01% total soluble protein for plants with p7017. See the table below for expression levels.

| Plasmid | Expression in callus[a] | Expression in leaf | Expression in T1 seed |
|---|---|---|---|
| p7017 | (not done) | 0.0007 | 0.044[b] (0.025) |
| p7699 | 0.01 | 0.085 | 0.011[c] |
| p7718 | 0.018 | 0.1 | 0.08[b] (0.055) |
| p8908 | (not done) | (not done) | 0.14[b] (0.12) |

[a] Expression levels are shown as percent total soluble protein
[b] Average of top four seeds (average of top seven seeds)
[c] Average of top three seeds only one low expressing event survived.

The laccase activity assay uses one of the mediators, ABTS (2,2-azino-bis-(3-ethylbenzthiazoline-6-sulfonic acid)) and can use a smaller or larger sample which increases the detectable amounts 100×. In this procedure, 0.2 ml of ABTS was introduced into a cuvette and 1.5 ml of NaOAc at a pH of 5.0 added. One blanks the cuvette, then 0.1 ml of the enzyme sample is added and mixed. Using a spectrophotometer, the change of absorption was measured at 420 nm, every 24 hours for 4 days. One ABTS unit is defined as a change of A420 per minute/2 provided the sample is not diluted.

The Enzyme Linked Immunosorbent Assay is performed on corn using anti-laccase polyclonal antibodies and alkaline phosphatase. The seed extracts are combined with buffering solution. After centrifugation and decanting, total protein concentration is assayed and adjusted to one concentration with PBST (phosphate buffered saline with 0.05% v/v polyoxyethylenesorbitan monolaureate (Tween-20)). Anti-laccase antibody-coated plates are used to capture laccase overnight at 4° C. Laccase standards are prepared and added to the wells along-side the test extracts. The plates are washed and diluted with biotinylated anti-laccase antibodies diluted with PBST. Following incubation, the plate is washed and streptavidin-alkaline phosphatase conjugate diluted with PBST is added and incubated. The plate is washed and pNPP substrate solution added and incubated. The plate is read and amount of target protein calculated by interpolation from the standard curve.

Details of the procedures used in these experiments is as follows. Nunc MaxiSorp 96-well microtiter plates, and an absorbance microplate reader were used. Coating antibodies used include purified IgG from rabbit; 0.05 M carbonate/bicarbonate coating buffer at pH 9.6; and PBST (phosphate-buffered saline with 0.05% Tween 20). The protein containing plant extract is standardized to 300 ng/$\mu$l. Additional materials included biotinylated rabbit secondary antibody; streptavidin-alkaline phosphatase (Jackson cat. No. 016-050-084); substrate buffer, pH 9.8; and pNpp substrate tablets.

The plates were coated by diluting the coating antibody 1:500 in the coating buffer. Protein was added at 100/ul per well, the plates covered and placed overnight at 4° C. on a flat surface. The next day, the plate was washed four times with PBST, patted dry and samples and standards added. To produce enough standards for four plates, the standard was diluted 1:100 in PBST (2 $\mu$l and 198 $\mu$l PBST) to get 3 ng/ul (X) as set forth below. 100 ul of each standard was added into wells in triplicate.

| | | |
|---|---|---|
| A | 3 ng | 30 μl of X, 2970 μl PBST |
| B | 1 ng | 750 μl of A, 1725 μl PBST |
| C | 0.3 ng | 200 μl of A, 1800 μl PBST |
| D | 0.1 ng | 200 μl of B, 1800 μl PBST |
| E | 0.06 ng | 125 μl of A, 1960 μl PBST |
| F | 0.03 ng | 200 μl of A, 1800 μl PBST |
| G | 0.01 ng | 200 μl of B, 1800 μl PBST |

Next, 90 μl of PBST was loaded to blank and sample wells. Up to 1.0 μg total protein was added for samples without signifiant interference with the standard curve. If more than 1.0 μg load was necessary, the standard curve was spiked with an identical amount of negative control corn seed protein. 10 μl PBST was loaded for buffer blank. A negative control corn seed extract was included on each plate. The plate was covered and incubated at 4° C. overnight on a flat surface.

The next day, the plate was washed four times with PBST and patted dry. A secondary antibody was diluted 1:10,000 in PBST. This was added at amounts of 100 ul per well, the wells covered and plates incubated at 37° C. for one hour. The plates were washed four times with PBST and patted dry. Streptavidin-alkaline phosphatase was diluted 1:50,000 in PBST. This was added at levels of 100 ul per well, covered and the plates incubated at 37° C. for one hour. The plates were washed four times with PBST and patted dry. Alkaline-phosphatase substrate solution was prepared by diluting tablets up to one tablet per 5 ml of substrate buffer. Once dissolved, 100 ul of substrate was added per well, covered and plates incubated at 37° C. for 30 minutes. After this time, the results were read at 405 nm on the absorbance microplate reader. The highest standard had OD around 0.8 to 1.1 and the blank ran at around 0.15 to 0.25.

Southern analysis is a well known technique to those skilled in the art. This common procedure involves isolating the plant DNA, cutting with restriction endonucleases and fractionating the cut DNA on an agarose gel to separate the DNA by molecular weight and transferring to nylon membranes. It is then hybridized with the probe fragment which was radioactively labeled with $^{32}$P and washed in an SDS solution. Southern, E., "Detection of a specific sequences among DNA fragments by gel electrophoresis" *J. Mol. Biol.* 98:503–517 (1975). Northern analysis is also a commonly used technique by those skilled in the art and is similar to Southern analysis except that RNA is isolated and placed on an agarose gel. The RNA is then hybridized with a labeled probe. Potter, E. et al. "Thyrotropin releasing hormone exerts rapid nuclear effects to increase production of the primary prolactin mRNA transcript" *Proc. Nat. Acad. Sci. U.S.A.* 78:6662–6666 (1981). A Western analysis is a variation of this technique, where instead of isolating DNA, the protein of interest is isolated and placed on an acrylamide gel. The protein is then blotted onto a membrane and contacted with a labeling substance. See e.g., Hood et al. "Commercial Production of Avidin from Transgenic Maize; Characterization of Transformants, Production, Processing, Extraction and Purification" *Molecular Breeding* 3:291–306 (1997).

Expression levels of laccase that are produced that are commercially attractive are as follows. While levels at about 0.01% are commercially useful; expression levels of 0.1% total soluble protein would be even more attractive, as it would allow recovery of 100 mg protein from 22 pounds of corn, which would cost approximately $1.20 to $2.00 for the processed corn. These figures become more commercially viable as expression levels increase. At levels of 1.0%, 100 mg of protein could be recovered from 2.2 pounds of corn at a cost of about $0.10 to 0.20 for the processed corn, and with levels of 10%, 100 mg of protein could be recovered from 0.22 pounds of corn at a cost of about $0.01–0.02 for the processed corn.

Thus it can be seen the invention accomplishes at least all of its objectives.

We claim:

1. A transgenic plant comprising a nucleotide sequence encoding laccase, operably linked to a promoter, wherein the laccase is preferentially expressed in the seed at levels of about 0.01% or higher of the total soluble protein of said plant.

2. The plant of claim 1, wherein the laccase is produced at levels of about 0.1% or higher of the total soluble protein of said plant.

3. The plant of claim 1, wherein the laccase is produced at levels of about 1% or higher of the total soluble protein of said plant.

4. The plant of claim 1, wherein the laccase is produced at levels of about 10% or higher of the total soluble protein of said plant.

5. The plant of claim 1, wherein the plant is corn.

6. The plant of claim 1, wherein the nucleotide sequence is a fungal nucleotide sequence.

7. The plant of claim 1, wherein the plant is maize, and wherein the nucleotide sequence is a Trametes versicolor nucleotide sequence.

8. The plant of claim 1, wherein the promoter is a globulin promoter.

9. Transformed seed of the plant of claim 1.

10. Transformed plant cells of the plant of claim 1.

11. A method of producing laccase in a plant comprising introducing into the plant a construct comprising a nucleotide encoding laccase operably linked to a promoter, wherein the laccase is preferentially expressed in the seed at levels of about 0.01% or higher of the total soluble protein of said plant, and extracting the laccase from the seed.

12. The method of claim 11, wherein the construct comprises a signal sequence which preferentially directing expression of the laccase to the plant.

13. The method of claim 11, wherein the promoter is a globulin promoter.

14. The method of claim 11, wherein the nucleotide sequence is a fungal nucleotide sequence.

15. The method of claim 11, wherein the plant is maize, and wherein the nucleotide sequence is a Trametes versicolor nucleotide sequence.

16. The plant of claim 1, wherein the plant is a monocotyledonous plant.

17. The seed of claim 9, wherein the seed plant is a monocotyledonous plant seed.

18. The plant cells of claim 10 wherein the plant cells are cells of a monocotyledonous plant.

19. The plant of claim 1 further comprising a signal sequence which preferentially directs expression of the laccase to the plant cell wall.

* * * * *

SEQUENCE LISTING

```
<160> NUMBER OF SEQ ID NOS: 3

<210> SEQ ID NO 1
<211> LENGTH: 1500
<212> TYPE: DNA
<213> ORGANISM: Trametes versicolor
<220> FEATURE:
<221> NAME/KEY: CDS
<222> LOCATION: (1)..(1497)

<400> SEQUENCE: 1 gcc atc ggg ccg gtg gcg agc ctc gtc gtc gcg aac gcc ccc gtc tcg      48
Ala Ile Gly Pro Val Ala Ser Leu Val Val Ala Asn Ala Pro Val Ser
  1               5                  10                  15 ccc gac ggc ttc ctt cgg gat gcc atc gtg gtc aac ggc gtg gtc cct      96
Pro Asp Gly Phe Leu Arg Asp Ala Ile Val Val Asn Gly Val Val Pro
             20                  25                  30 tcc ccg ctc atc acc ggg aag aag gga gac cgc ttc cag ctc aac gtc     144
Ser Pro Leu Ile Thr Gly Lys Lys Gly Asp Arg Phe Gln Leu Asn Val
         35                  40                  45 gtc gac acc ttg acc aac cac agc atg ctc aag tcc act agt atc cac     192
Val Asp Thr Leu Thr Asn His Ser Met Leu Lys Ser Thr Ser Ile His
     50                  55                  60
```

-continued

| | | |
|---|---|---|
| tgg cac ggc ttc ttc cag gca ggc acc aac tgg gca gac gga ccc gcg<br>Trp His Gly Phe Phe Gln Ala Gly Thr Asn Trp Ala Asp Gly Pro Ala<br>65                          70                     75                      80 | 240 |
| ttc gtc aac cag tgc cct att gct tcc ggg cat tca ttt ctg tac gac<br>Phe Val Asn Gln Cys Pro Ile Ala Ser Gly His Ser Phe Leu Tyr Asp<br>85                     90                     95 | 288 |
| ttc cat gtg ccc gac cag gca gga acg ttc tgg tac cac agt cat ctg<br>Phe His Val Pro Asp Gln Ala Gly Thr Phe Trp Tyr His Ser His Leu<br>100                     105                     110 | 336 |
| tct acg caa tac tgt gac ggg ctg cga gga ccg ttc gtc gtg tac gac<br>Ser Thr Gln Tyr Cys Asp Gly Leu Arg Gly Pro Phe Val Val Tyr Asp<br>115                     120                     125 | 384 |
| ccc aag gat ccg cac gcc agc cgc tac gat gtt gac aac gag agc acg<br>Pro Lys Asp Pro His Ala Ser Arg Tyr Asp Val Asp Asn Glu Ser Thr<br>130                     135                     140 | 432 |
| gtc atc acg ttg acc gac tgg tac cac acc gct gcc cgg ctc ggt ccc<br>Val Ile Thr Leu Thr Asp Trp Tyr His Thr Ala Ala Arg Leu Gly Pro<br>145                     150                     155                     160 | 480 |
| agg ttc cca ctc ggc gcg gac gcc acg ctc atc aat ggt ctt ggg cgg<br>Arg Phe Pro Leu Gly Ala Asp Ala Thr Leu Ile Asn Gly Leu Gly Arg<br>                        165                     170                     175 | 528 |
| tcg gcc tcc act ccc acc gcc gcg ctt gct gtg atc aac gtc cag cac<br>Ser Ala Ser Thr Pro Thr Ala Ala Leu Ala Val Ile Asn Val Gln His<br>                        180                     185                     190 | 576 |
| gga aag cgc tac cgc ttc cgt ctc gtt tcg atc tcg tgc gac ccg aac<br>Gly Lys Arg Tyr Arg Phe Arg Leu Val Ser Ile Ser Cys Asp Pro Asn<br>                    195                     200                     205 | 624 |
| tac acg ttc agc atc gac ggg cac aat ctg acc gtc atc gag gtc gac<br>Tyr Thr Phe Ser Ile Asp Gly His Asn Leu Thr Val Ile Glu Val Asp<br>210                     215                     220 | 672 |
| ggt atc aac agc cag cct ctc ctt gtc gac tct atc cag atc ttc gcc<br>Gly Ile Asn Ser Gln Pro Leu Leu Val Asp Ser Ile Gln Ile Phe Ala<br>225                     230                     235                     240 | 720 |
| gcg cag cgc tac tcc ttt gtg ttg aat gcg aac caa acg gtc ggc aac<br>Ala Gln Arg Tyr Ser Phe Val Leu Asn Ala Asn Gln Thr Val Gly Asn<br>                        245                     250                     255 | 768 |
| tac tgg gtc cgc gcg aac ccg aac ttc gga acg gtt ggg ttc gcc ggg<br>Tyr Trp Val Arg Ala Asn Pro Asn Phe Gly Thr Val Gly Phe Ala Gly<br>                    260                     265                     270 | 816 |
| ggg atc aac tcc gcc atc ctg cgc tac caa ggc gca cca gtc gcc gag<br>Gly Ile Asn Ser Ala Ile Leu Arg Tyr Gln Gly Ala Pro Val Ala Glu<br>                    275                     280                     285 | 864 |
| ccc act acg acc cag acg acg tcg gtg atc ccg ctt atc gag acg aac<br>Pro Thr Thr Thr Gln Thr Thr Ser Val Ile Pro Leu Ile Glu Thr Asn<br>290                     295                     300 | 912 |
| ttg cac ccc ctc gct cgc atg cct gtg cct ggc agc ccg aca ccc ggg<br>Leu His Pro Leu Ala Arg Met Pro Val Pro Gly Ser Pro Thr Pro Gly<br>305                     310                     315                     320 | 960 |
| ggc gtc gac aag gcg ctc aac ctc gcg ttt aac ttc aac ggc acc aac<br>Gly Val Asp Lys Ala Leu Asn Leu Ala Phe Asn Phe Asn Gly Thr Asn<br>                    325                     330                     335 | 1008 |
| ttc ttc atc aac aac gcg act ttc acg ccg ccg acc gtc ccg gta ctc<br>Phe Phe Ile Asn Asn Ala Thr Phe Thr Pro Pro Thr Val Pro Val Leu<br>340                     345                     350 | 1056 |
| ctc cag att ctg agc ggt gcg cag acc gca caa gac ctg ctc cct gca<br>Leu Gln Ile Leu Ser Gly Ala Gln Thr Ala Gln Asp Leu Leu Pro Ala<br>                    355                     360                     365 | 1104 |
| ggc tct gtc tac ccg ctc ccg gcc cac tcc acc atc gag atc acg ctg<br>Gly Ser Val Tyr Pro Leu Pro Ala His Ser Thr Ile Glu Ile Thr Leu<br>370                     375                     380 | 1152 |

```
ccc gcg acc gcc ttg gcc ccg ggt gca ccg cac ccc ttc cac ctg cac      1200
Pro Ala Thr Ala Leu Ala Pro Gly Ala Pro His Pro Phe His Leu His
385                 390                 395                 400 ggt cac gcc ttc gcg gtc gtt cgc agc gcg ggg agc acc acg tat aac      1248
Gly His Ala Phe Ala Val Val Arg Ser Ala Gly Ser Thr Thr Tyr Asn
                405                 410                 415 tac aac gac ccg atc ttc cgc gac gtc gtg agc acg ggc acg ccc gcc      1296
Tyr Asn Asp Pro Ile Phe Arg Asp Val Val Ser Thr Gly Thr Pro Ala
            420                 425                 430 gcg ggc gac aac gtc acg atc cgc ttc cag acg gac aac ccc ggg ccg      1344
Ala Gly Asp Asn Val Thr Ile Arg Phe Gln Thr Asp Asn Pro Gly Pro
                435                 440                 445 tgg ttc ctc cac tgc cac atc gac ttc cac ctc gac gcg ggc ttc gcg      1392
Trp Phe Leu His Cys His Ile Asp Phe His Leu Asp Ala Gly Phe Ala
    450                 455                 460 atc gtg ttc gca gag gac gtt gcg gac gtg aag gcg gcg aac ccg gtt      1440
Ile Val Phe Ala Glu Asp Val Ala Asp Val Lys Ala Ala Asn Pro Val
465                 470                 475                 480 ccg aag gcg tgg tcg gac ctg tgc ccg atc tac gac ggg ctg agc gag      1488
Pro Lys Ala Trp Ser Asp Leu Cys Pro Ile Tyr Asp Gly Leu Ser Glu
                485                 490                 495 gct aac cag tga                                                      1500
Ala Asn Gln
```

<210> SEQ ID NO 2
<211> LENGTH: 499
<212> TYPE: PRT
<213> ORGANISM: Trametes versicolor

<400> SEQUENCE: 2

```
Ala Ile Gly Pro Val Ala Ser Leu Val Val Ala Asn Ala Pro Val Ser
 1               5                  10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
            35                  40                  45

Val Asp Thr Leu Thr Asn His Ser Met Leu Lys Ser Thr Ile His
     50                  55                  60

Trp His Gly Phe Phe Gln Ala Gly Thr Asn Trp Ala Asp Gly Pro Ala
65                  70                  75                  80

Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
        130                 135                 140

Val Ile Thr Leu Thr Asp Trp Tyr His Thr Ala Ala Arg Leu Gly Pro
145                 150                 155                 160

Arg Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
        195                 200                 205
```

-continued

| | | | | | | | | | | | | | | |
|---|---|---|---|---|---|---|---|---|---|---|---|---|---|---|
|Tyr|Thr|Phe|Ser|Ile|Asp|Gly|His|Asn|Leu|Thr|Val|Ile|Glu|Val|Asp|
| |210| | | |215| | | |220| | | | | | |

Tyr Thr Phe Ser Ile Asp Gly His Asn Leu Thr Val Ile Glu Val Asp
        210             215             220

Gly Ile Asn Ser Gln Pro Leu Leu Val Asp Ser Ile Gln Ile Phe Ala
225             230             235             240

Ala Gln Arg Tyr Ser Phe Val Leu Asn Ala Asn Gln Thr Val Gly Asn
            245             250             255

Tyr Trp Val Arg Ala Asn Pro Asn Phe Gly Thr Val Gly Phe Ala Gly
        260             265             270

Gly Ile Asn Ser Ala Ile Leu Arg Tyr Gln Gly Ala Pro Val Ala Glu
            275             280             285

Pro Thr Thr Thr Gln Thr Thr Ser Val Ile Pro Leu Ile Glu Thr Asn
        290             295             300

Leu His Pro Leu Ala Arg Met Pro Val Pro Gly Ser Pro Thr Pro Gly
305             310             315             320

Gly Val Asp Lys Ala Leu Asn Leu Ala Phe Asn Phe Asn Gly Thr Asn
            325             330             335

Phe Phe Ile Asn Asn Ala Thr Phe Thr Pro Thr Val Pro Val Leu
            340             345             350

Leu Gln Ile Leu Ser Gly Ala Gln Thr Ala Gln Asp Leu Leu Pro Ala
            355             360             365

Gly Ser Val Tyr Pro Leu Pro Ala His Ser Thr Ile Glu Ile Thr Leu
370             375             380

Pro Ala Thr Ala Leu Ala Pro Gly Ala Pro His Pro Phe His Leu His
385             390             395             400

Gly His Ala Phe Ala Val Val Arg Ser Ala Gly Ser Thr Thr Tyr Asn
            405             410             415

Tyr Asn Asp Pro Ile Phe Arg Asp Val Val Ser Thr Gly Thr Pro Ala
            420             425             430

Ala Gly Asp Asn Val Thr Ile Arg Phe Gln Thr Asp Asn Pro Gly Pro
            435             440             445

Trp Phe Leu His Cys His Ile Asp Phe His Leu Asp Ala Gly Phe Ala
        450             455             460

Ile Val Phe Ala Glu Asp Val Ala Asp Val Lys Ala Ala Asn Pro Val
465             470             475             480

Pro Lys Ala Trp Ser Asp Leu Cys Pro Ile Tyr Asp Gly Leu Ser Glu
            485             490             495

Ala Asn Gln

<210> SEQ ID NO 3
<211> LENGTH: 1401
<212> TYPE: DNA
<213> ORGANISM: Zea mays
<220> FEATURE:
<223> OTHER INFORMATION: Globulin-1 promoter

<400> SEQUENCE: 3
aagcttgccg agtgccatcc ttggacactc gataaagtat attttatttt ttttattttg      60
ccaaccaaac tttttgtggt atgttcctac actatgtaga tctacatgta ccattttggc     120
acaattacat atttacaaaa atgttttcta taatattag atttagttcg tttatttgaa      180
tttcttcgga aaattcacat ttaaactgca agtcactcga acatggaaa accgtgcatg      240 caaaataaat gatatgcatg ttatctagca caagttacga ccgatttcag aagcagacca     300
gaatcttcaa gcaccatgct cactaaacat gaccgtgaac ttgttatcta gttgtttaaa     360
aattgtataa aacacaaata aagtcagaaa ttaatgaaac ttgtccacat gtcatgatat     420

```
catatataga ggttgtgata aaaatttgat aatgtttcgg taaagttgtg acgtactatg    480
tgtagaaacc taagtgacct acacataaaa tcatagagtt tcaatgtagt tcactcgaca    540
aagactttgt caagtgtccg ataaaaagta ctcgacaaag aagccgttgt cgatgtactg    600
ttcgtcgaga tctctttgtc gagtgtcaca ctaggcaaag tctttacgga gtgttttca     660 ggctttgaca ctcggcaaag cgctcgattc cagtagtgac agtaatttgc atcaaaaata    720
gctgagagat ttaggccccg tttcaatctc acgggataaa gtttagcttc ctgctaaact    780
ttagctatat gaattgaagt gctaaagttt agtttcaatt accaccatta gctctcctgt    840
ttagattaca aatggctaaa agtagctaaa aaatagctgc taaagtttat ctcgcgagat    900
tgaaacaggg ccttaaaatg agtcaactaa tagaccaact aattattagc tattagtcgt    960
tagcttcttt aatctaagct aaaaccaact aatagcttat ttgttgaatt acaattagct   1020
caacggaatt ctctgttttt ctaaaaaaaa actgcccctc tcttacagca aattgtccgc   1080
tgcccgtcgt ccagatacaa tgaacgtacc tagtaggaac tcttttacac gctcggtcgc   1140
tcgccgcgga tcggagtccc cggaacacga caccactgtg gaacacgaca aagtctgctc   1200
agaggcggcc acaccctggc gtgcaccgag ccggagcccg gataagcacg gtaaggagag   1260
tacggcggga cgtggcgacc cgtgtgtctg ctgccacgca gccttcctcc acgtagccgc   1320
gcggccgcgc cacgtaccag ggcccggcgc tggtataaat gcgcgccacc tccgctttag   1380
ttctgcatac agccaaccca a                                             1401
```